US009155902B2

(12) United States Patent
Schwibner et al.

(10) Patent No.: US 9,155,902 B2
(45) Date of Patent: Oct. 13, 2015

(54) POCKET KITS AND METHODS FOR RETROFITTING AND ADAPTING COMMON NOTEBOOK COMPUTERS, LAPTOP COMPUTERS, AND TABLET COMPUTERS, TO ENABLE EACH TO BE USED AS AN AUTOMATED EXTERNAL DEFIBRILLATOR (AED), AND AS A MANUAL DEFIBRILLATOR

(71) Applicant: BABRIC LIFE SCIENCE INNOVATIONS, LLC., Boca Raton, FL (US)

(72) Inventors: Barry H. Schwibner, Boca Raton, FL (US); Brad Schwartz, Boca Raton, FL (US); Eric Judge, Boca Raton, FL (US)

(73) Assignee: CompToLife, LLC, Boca Raton, FL (US)

( * ) Notice: Subject to any disclaimer, the term of this patent is extended or adjusted under 35 U.S.C. 154(b) by 0 days.

(21) Appl. No.: 14/073,528

(22) Filed: Nov. 6, 2013

(65) Prior Publication Data

US 2014/0067001 A1    Mar. 6, 2014

Related U.S. Application Data

(60) Division of application No. 13/633,753, filed on Oct. 2, 2012, now Pat. No. 8,594,784, which is a continuation-in-part of application No. 12/709,905, filed on Feb. 22, 2010.

(60) Provisional application No. 61/154,013, filed on Feb. 20, 2009.

(51) Int. Cl.
*A61N 1/39*     (2006.01)

(52) U.S. Cl.
CPC ............. *A61N 1/3968* (2013.01); *A61N 1/3993* (2013.01)

(58) Field of Classification Search
USPC ............................................................ 607/5
See application file for complete search history.

(56) References Cited

U.S. PATENT DOCUMENTS

| 5,097,830 A | 3/1992 | Eikefjord et al. |
| 5,666,006 A | 9/1997 | Townsley et al. |

(Continued)

FOREIGN PATENT DOCUMENTS

WO       0195454 A1     12/2001

OTHER PUBLICATIONS

Page R., et al.; "Biphasic Versus Monophasic Shock Waveform for Conversion of Atrial Fibrillation"; Journal of the American College of Cardiology. 2002; 39:1956-1963.

(Continued)

*Primary Examiner* — Paula J Stice
(74) *Attorney, Agent, or Firm* — Whitmyer IP Group LLC

(57) ABSTRACT

A notebook, laptop computer or tablet computer having an automated external defibrillator (AED) capability, and methods of utilizing the notebook, laptop computer or tablet computer defibrillator to treat victims of sudden cardiac arrest. Kits and methods for converting, adapting or retrofitting a common notebook, laptop computer and tablet computer to enable each to be used as an AED to treat victims of sudden cardiac arrest. A kit including an adjustable case for receiving, encompassing, adapting and converting a common notebook, laptop computer or tablet computer to enable each to be used as an AED. A kit including a slave automated external defibrillator (AED) that is joined to a common notebook, laptop computer or tablet computer to adapt, convert and enable each to be used as an AED.

25 Claims, 6 Drawing Sheets

(56) References Cited

U.S. PATENT DOCUMENTS

| | | | |
|---|---|---|---|
| 5,782,878 A | 7/1998 | Morgan et al. | |
| 5,933,551 A | 8/1999 | Boudreau et al. | |
| 6,141,584 A | 10/2000 | Rockwell et al. | |
| 6,292,692 B1 | 9/2001 | Skelton et al. | |
| 6,323,621 B1 | 11/2001 | Jacobs | |
| 6,398,744 B2 | 6/2002 | Bystrom et al. | |
| 6,422,669 B1 | 7/2002 | Salvatori et al. | |
| 6,603,999 B2 | 8/2003 | SerVaas | |
| 6,655,528 B2 | 12/2003 | King | |
| 7,006,865 B1 | 2/2006 | Cohen et al. | |
| 7,873,416 B2 | 1/2011 | Guo et al. | |
| 2002/0183790 A1* | 12/2002 | Sullivan et al. | 607/5 |
| 2003/0028219 A1* | 2/2003 | Powers et al. | 607/5 |
| 2003/0233129 A1* | 12/2003 | Matos | 607/5 |
| 2004/0122476 A1 | 6/2004 | Wung | |
| 2005/0159782 A1 | 7/2005 | Powers et al. | |
| 2005/0192640 A1 | 9/2005 | Ousdigian et al. | |
| 2005/0277872 A1 | 12/2005 | Colby, Jr. et al. | |
| 2006/0149321 A1* | 7/2006 | Merry et al. | 607/5 |
| 2006/0173501 A1 | 8/2006 | Stickney et al. | |
| 2007/0270909 A1 | 11/2007 | Saketkhou | |
| 2007/0299473 A1 | 12/2007 | Matos | |
| 2008/0140140 A1* | 6/2008 | Grimley et al. | 607/5 |
| 2008/0177341 A1 | 7/2008 | Bowers | |
| 2009/0108162 A1 | 4/2009 | Hatton | |
| 2011/0046688 A1 | 2/2011 | Schwibner et al. | |

OTHER PUBLICATIONS

Eisenberg M, et al; "Cardiac Resuscitation"; NEJM 2001; 344:1304-1313, Apr. 26, 2001.

Atkins DL.; "Public access defibrillation: Where does it work?" Circulation. 2009;120:461-463.

International Search Report and Written Opinion of the International Searching Authority Application No. PCT/US2013/062952 Completed: Dec. 19, 2013; Mailing Date: Dec. 30, 2013 16 pages.

* cited by examiner

POCKET KITS AND METHODS FOR RETROFITTING AND ADAPTING COMMON NOTEBOOK COMPUTERS, LAPTOP COMPUTERS, AND TABLET COMPUTERS, TO ENABLE EACH TO BE USED AS AN AUTOMATED EXTERNAL DEFIBRILLATOR (AED), AND AS A MANUAL DEFIBRILLATOR

FIELD OF THE INVENTION

The present invention relates to a notebook, laptop computer and tablet computer having an automated external defibrillator (AED) capability, and methods of adapting and utilizing the notebook, laptop computer and tablet computer defibrillator to treat victims of sudden cardiac arrest. The present invention also involves methods for implementing the common notebook, laptop computer and tablet computer as an automated external defibrillator (AED).

The present invention further relates to kits and methods for converting, adapting or retrofitting a common notebook, laptop computer and tablet computer to enable each to be used as an AED to treat victims of sudden cardiac arrest. The present invention describes an adjustable universal case, receptacle, holder or frame with an integrated AED for receiving, encompassing, adapting and converting a common notebook, laptop computer or tablet computer to enable each to be used as an AED.

The present invention also relates to a kit, which consists of a "slave" AED that is joined to a common notebook, laptop computer or tablet computer to adapt, convert and enable each to be used as an AED.

BACKGROUND OF THE INVENTION

Cardiac arrest occurs when a person's heart stops beating. This may occur when a person dies from illness or injury, or it may occur abruptly and unexpectedly. In this latter case, abrupt and unexpected cardiac arrest is referred to as sudden cardiac arrest, and is often associated with coronary heart disease (CHD). The most common cause of sudden cardiac arrest is a heart attack that results from ventricular fibrillation (VF), whereby a person has a severely abnormal heart rhythm that causes quivering of the heart's lower chambers and causes the heart to suddenly stop pumping blood. Additionally, sudden cardiac arrest can also be caused by the extreme slowing of the heart, known as bradycardia, and by the heart beating too fast, known as tachycardia. All conditions that cause the heart to suddenly stop pumping blood can be life threatening.

A victim of ventricular fibrillation sudden cardiac arrest may or may not have diagnosed heart disease. Under certain conditions, various heart medications and other drugs, as well as illegal drug abuse, can lead to abnormal heart rhythms that cause cardiac arrest and sudden death. Other causes of cardiac arrest include respiratory arrest, electrocution, drowning, choking and trauma, and cardiac arrest can also occur without any known cause.

Typically, when VF sudden cardiac arrest occurs, a victim suddenly collapses, is unresponsive to gentle shaking, stops normal breathing, and after two rescue breaths, has no sign of circulation such as normal breathing, coughing or movement. Death can occur within minutes if the victim receives no treatment. Brain damage can start to occur in just 4 to 6 minutes after the heart stops pumping blood.

Once VF sudden cardiac arrest occurs, death or permanent damage may be averted if the sudden cardiac arrest victim receives immediate bystander cardiopulmonary resuscitation (CPR) and defibrillation to reverse VF sudden cardiac arrest. This involves treating the victim with an electric shock to the heart within minutes. The electric shock can stop the abnormal rhythm of the heart and can allow a normal rhythm of the heart to resume. This process, called defibrillation, is done through use of a defibrillator. Lay people can, and have been trained to operate defibrillators, many of which are known as portable, automated external defibrillators (AEDs).

AEDs, as they currently exist, are safe for lay rescuers to treat sudden cardiac arrest because the devices automatically analyze a victim's heart rhythm, and only allow an electric shock to be delivered when necessary. In their present state, when available, AEDs are easy to use, compact, battery operated, lightweight and durable.

At present the probability of a victim surviving VF sudden cardiac arrest is dependent, to a large degree, on whether the sudden cardiac arrest occurs in the immediate vicinity of an AED, and whether the episode is witnessed by a bystander, who is familiar with both the administration of CPR, and with the use of an AED. By today's standards, response times have been improved, but to a limited extent, by placing AEDs strategically, in public buildings, arenas, and emergency vehicles. In recent years, with the advent of the portable AED, many portable AED devices have been purchased for placement in homes by people with a prior history of a heart attack, or with a history of coronary heart disease. An important point to be noted, however, is that 50 percent of men and 63 percent of women who died suddenly of coronary heart disease had no previous symptoms of this disease.

Additionally, it is estimated that about 95% of sudden cardiac arrest victims die before reaching the hospital. Survival is directly linked to the amount of time between the onset of sudden cardiac arrest and defibrillation. If no bystander CPR is provided, a victim's chance of survival is reduced by 7 to 10 percent with every minute of delay until defibrillation. The VF sudden cardiac arrest survival rate is only two to five percent if defibrillation is provided more than 12 minutes after collapse.

The average time from collapse to beginning CPR to providing defibrillation varies widely across the United States. Communities that train in CPR, and strategically place AEDs in public buildings, arenas, and emergency vehicles can significantly reduce response times. Some studies show, for example, that police equipped with AEDs can cut response time to sudden cardiac arrest victims by about three minutes compared to historical response times.

The current "state of the art" is public access defibrillation (PAD); or posted automated external defibrillators (AED's) in airports and other transportation centers, schools, large shopping malls, sports complexes, large industrial sites, and other public places. However, these posted AEDs are not always where they are needed. There are cases in which witnesses to cardiac arrests are unable to locate posted AEDs. In other instances, posted AEDs are located, and found only to have expired batteries and/or electrodes. Moreover, posted AEDs suffer from various maintenance issues.

Referring to public access defibrillation (PAD); an article titled, "Public Access Defibrillation . . . Where Does It Work?" appearing in the *Journal, Circulation* (of the American Medical Association) by Dr. Diane Atkins, of the University of Iowa Children's Hospital and the Carver College of Medicine; clearly states, "that the mere presence of an AED in the general area of an arrest does not guarantee success". Dr. Atkins also states, "in addition to the optimal placement of AEDs, an effective PAD program requires continued supervision, maintenance, and training. Over time, it is likely that the supervision and maintenance of a PAD site may falter, especially if the site is maintained by volunteers". The article continues, "two years after placement, none of the sites had successfully maintained the program as judged by the AHA (*American Heart Association*) recommendations, earning only a mean of 57% of the possible points. On-site interviews detected problems with access, unapparent location of the AED, and inoperative equipment such as expired pads or batteries". See Atkins DL. Public access defibrillation: Where does it work? *Circulation*. 2009; 120:461-463.

A study of division 1 National Collegiate Athletic Association programs found similar results. Most AEDs had been purchased for concerns of liability, with no determination of local EMS response times, geography of the sports facilities, or budgetary planning. Maintenance checks were more than every 6 months or unknown in 30% of the schools. Thus, placement in high-risk locations alone does not ensure that the AED will be operative or used when needed." See Coris E, Miller E, Sahebzamani F. Sudden cardiac death in division I collegiate athletics: analysis of automated external defibrillator utilization in National Collegiate Athletic Association division I athletic programs. Clin J Sports Med. 2005; 15:87-91.

A recurring criticism in the literature of the status quo PAD (Public Access Defibrillation) is the general lack of regulatory over-site (federal, state or local) and no prescribed standards for starting a PAD program and no prescribed standards for maintaining a PAD program.

So for today's victims of VF sudden cardiac arrest, current standards and availability of AEDs limit survival chances to what basically approaches the equivalent of "a roll of the dice" or "the luck of the draw". This is extremely troubling when one considers that people die from VF sudden cardiac arrest every hour of every day, throughout the world.

Furthermore, early CPR, and rapid defibrillation combined with early advanced care can produce high long-term survival rates. When bystanders provide immediate CPR, and the first shock is delivered within 3 to 5 minutes, the reported survival rates from ventricular fibrillation sudden cardiac arrest are as high as 48 to 74 percent. No statistics are available for the exact number of sudden cardiac arrests that occur each year. However, about 335,000 people a year die of coronary heart disease without being hospitalized. This equates to about 918 Americans each day. This is now the third-leading cause of death behind cancer and non-sudden cardiovascular deaths.

Studies have shown that when bystanders perform effective CPR immediately after sudden cardiac arrest, they can double a victim's chance of survival. Additionally, about 80 percent of all cardiac arrests occur at home and almost 60 percent are witnessed. Thus, there is a societal need to treat victims of VF sudden cardiac arrest by providing portable AED devices. There is a societal need to provide portable AED devices that can be quickly accessed. There is an additional societal need to provide portable AED devices that are part of customary computer devices that people keep with their person or in their homes, as well as computer devices that are provided to first responders.

A prior art reference, U.S. Patent Publication No. 2007/0270909 (Saketkhou), is directed to providing an AED in a cell phone or a mobile phone. However, Saketkhou does not teach adapting a common notebook, laptop computer, or tablet computer, to adapt, convert, and enable each to be used as an automated external defibrillator (AED).

Saketkhou does not teach methods of adapting and utilizing a notebook, laptop computer or tablet computer defibrillator to treat victims of sudden cardiac arrest. The common notebook, laptop computer and tablet computer differ from PDAs and cell phones, with regards to size, processing power, and portability. As defined in http://en.wikipedia.org/wiki/Laptop, a notebook computer is a personal computer for mobile use that includes a display, a keyboard, and a pointing device (a touchpad, also known as a trackpad or pointing stick) in a single unit. Additionally, computers typically contain a full keyboard having buttons which are typically wider than a person's finger. In contrast, cell phones do not have full keyboards and PDAs do not typically have a keyboard at all, and rather use a stylus, such as a pen.

Furthermore, the common notebook, laptop computer and tablet computer are typically available to first responders, such as policemen, firefighters, paramedics and emergency medical technicians (EMTs). The common notebook, laptop computer and tablet computer have greater processing power than mobile phones and are typically included as an apparatus of a first responder.

SUMMARY OF THE INVENTION

Thus, it is desirable to provide a portable AED device that is easy to use, compact, battery operated, lightweight and durable, while is capable to be implemented as part of customary electronic devices such as a computer, laptop computer, notebook computer and tablet computer, because it satisfies a long-felt need to provide portable AED devices in computers. There is a need to provide access to AED devices to bystanders aiding victims that suffer from sudden cardiac arrest, where bystanders do not typically have access to AED devices and victims die before reaching a hospital.

It is also desirable to provide a retrofit to a common computer, laptop computer, notebook computer or tablet computer that allows for a portable AED to be attached to or incorporated within, about or around the computer, laptop computer, notebook computer or tablet computer.

It is also desirable to provide a slave device that connects to a common computer, laptop computer, notebook computer or tablet computer that allows for a portable AED to be present within the slave device, and where slave device is in communication with the computer, so that the portable AED in the slave device can be used to administer defibrillation shocks to a patient.

It is desirable for a computer, laptop computer, notebook or tablet computer to incorporate a portable AED (automated external defibrillator) device as well as cables and electrode pads within a compartment in the portable AED (automated external defibrillator) device. It is desirable for the cables or leads and electrode pads to be detachable, but connected to the defibrillator element in the portable AED (automated external defibrillator) device to enable replacement upon expiration and/or upon a defect alert, both provided by the retrofitted laptop, notebook or tablet computer. The cables and electrode pads fit within a compartment having a lid or flap, such that the cables and electrode pads are stored within the compartment. This is important as once the compartment is opened, the electrode pads will be free to be applied to a victim suffering from VF sudden cardiac arrest. This prevents the delay, as in existing AEDs, whereby a user must connect the cables to the defibrillator element before applying the electrode pads to the victim. Also this prevents instances where the electrode pads and cables become separated from the defibrillator device. Requiring one to connect cables and electrode pads to the defibrillator results in the loss of critical time, time which is vital to improve the chances of survival of the victim.

It is also desirable to provide a portable AED (automated external defibrillator) device where a defibrillator control is provided in a compartment within the device. It is desirable for the defibrillator control to only be accessible if a user enters a password or key word into the device allowing the user to access the defibrillator control located within a compartment. This provides a safety mechanism whereby accidental use of the defibrillator element is minimized.

The present invention seeks to achieve overcoming the desired deficiencies in the prior art.

Accordingly, it is an object of the present invention to include providing an automated external defibrillator (AED) capability to the millions of new and after-market medical computers, such as mobile clinical assistants (MCAs), currently in use and carried by physicians, nurses and staff members in offices and hospitals throughout the world. With the current trend toward electronic medical records (EMRs), these devices are now commonplace and a vital part of the current armamentarium throughout the medical profession.

Potential applications of the present invention include retrofitting the millions of new and after-market mobile clinical assistants (MCAs) currently in use and providing and retrofitting "rugged" laptops and tablet computers used by the military, law enforcement, emergency medical technicians (EMTs), paramedics and other medical support staff.

Accordingly, it is an object of the present invention to incorporate a defibrillator into a computer, laptop, notebook and tablet computer (such as an iPad®). It is another object of the invention to retrofit laptops and tablet computers used by the military, law enforcement, emergency medical technicians (EMTs), paramedics and other medical support staff.

It is another object of the present invention to incorporate a modified form of current portable automated external defibrillator (AED) technology into a kit. It is another object of the present invention to provide methods for converting, adapting or retrofitting a common notebook, laptop computer and tablet computer to enable each to be used as an automated external defibrillator (AED) to treat victims of sudden cardiac arrest.

It is another object of the present invention to provide various kits for converting, adapting or retrofitting a common notebook, laptop computer and tablet computer to enable each to be used as an automated external defibrillator (AED) to treat victims of sudden cardiac arrest.

It is another object of the present invention to provide a slave device that connects to a common computer, laptop computer, notebook computer or tablet computer that allows for a portable AED to be present within the slave device, and where slave device is in communication with the computer, so that the portable AED in the slave device can be used to administer defibrillation shocks to a patient.

These and other objectives are achieved by providing a method for retrofitting a computer with a defibrillator, the method comprising the steps of: providing a computer; providing an adjustable case for receiving the computer, the adjustable case including a defibrillator element, the defibrillator element including at least one cable and at least one electrode pad, the at least one cable and at least one electrode pad being located within a compartment in the adjustable case; attaching the computer to the adjustable case; and electronically linking the computer to the defibrillator element in the adjustable case, so that the computer controls the defibrillator element during use of the defibrillator element.

In certain embodiments, the step of attaching the computer to the adjustable case involves placing the computer within the adjustable case.

In certain embodiments, the adjustable case is composed of four L-shaped members. In certain embodiments, each of the four L-shaped members fit over each of the four corners of the computer. In certain embodiments, each of the four L-shaped members have a length and a width, and each of the four L-shaped members are adjustable so that the length and width of the four L-shaped members vary to accommodate the dimensions of the computer.

In certain embodiments, the method further involves providing a defibrillator control element, the defibrillator control element being housed within an additional compartment in the adjustable case. In certain embodiments, the defibrillator control element is only accessed upon entering a password or key code into the computer.

In certain embodiments, the adjustable case is linked to the computer via an electronic connector component.

In certain embodiments, the electronic connector component is selected from a group consisting of a USB cable, a cable wire, port adaptors, a Y-shaped cable, two USB connectors or BLUETOOTH. As defined herein, BLUETOOTH is a wireless technology standard for exchanging data over short distances (using short-wavelength radio transmissions in the ISM band from 2400-2480 MHz). As defined herein, USB is an industry standard developed in the mid-1990s that defines the cables, connectors and communications protocols used in a bus for connection, communication and power supply between computers and electronic devices.

In certain embodiments, the adjustable case includes an external chip, the external chip required to access the defibrillator element. In certain embodiments, to receive the external chip, a user must first complete a training program covering CPR and defibrillation.

In certain embodiments, the computer is selected from a group consisting of a notebook computer, a laptop computer or a tablet computer.

In certain embodiments, the defibrillator element further includes a power source.

In certain embodiments, the notebook and the laptop each include a display, a keyboard and a pointing device. In certain embodiments, the defibrillator element within the adjustable case provides low energy shocks of 120-200 joules. In certain embodiments, the at least one cable and at least one electrode pad are connected or detachably attached to the defibrillator element within the adjustable case. In certain embodiments the at least one cable and at least one electrode pad are detachable from the defibrillator element within the adjustable case, to enable replacement upon expiration and/or upon a defect alert, both provided by the retrofitted computer, laptop computer, notebook computer or tablet computer.

Other objects of the invention are achieved by providing a kit for retrofitting a computer with an external defibrillator, the kit comprising: an adjustable case for receiving a computer, the adjustable case including a defibrillator element, the defibrillator element having at least one cable and at least one electrode pad, the at least one cable and at least one electrode pad being housed in a compartment in the adjustable case; and an electronic connector component, the electronic connector component connecting the defibrillator element to the computer, so that the computer controls the defibrillator element during use of the defibrillator element.

In certain embodiments, the adjustable case is composed of four L-shaped members. In certain embodiments, each of the four L-shaped members fit over a corner of the computer. In certain embodiments, each of the four L-shaped members have a length and a width, and each of the four L-shaped members are adjustable so that the length and width of the four L-shaped members vary to accommodate the computer.

In certain embodiments, the defibrillator element provides low energy shocks of 120-200 joules.

In certain embodiments, the adjustable case further comprises a defibrillator control element, the defibrillator control element being housed within an additional compartment in the adjustable case. In certain embodiments, the defibrillator control element may only be accessed upon entering a password or key code into the computer.

In certain embodiments, the electronic connector component is selected from a group consisting of a USB cable, a cable wire, port adaptors, a Y-shaped cable, two USB connectors or BLUETOOTH.

In certain embodiments, the computer is selected from a group consisting of a notebook, a laptop computer or a tablet computer.

In certain embodiments, the adjustable case further comprises a manual over-ride, the manual over-ride providing the ability to administer a defibrillating shock from the defibrillator element. The manual over-ride allows a medical professional to bypass the automated component of the AED (automated external defibrillator); which when in automated mode proceeds with an analysis of the sudden cardiac arrest victim's heart rhythm. The manual over-ride provides a saving of time for the medical professional who may elect to defibrillate without automated heart rhythm analysis. The manual over-ride allows a medical professional to administer a defibrillating shock from the defibrillator element, even though the proper access code is not entered into the computer. In certain embodiments, the manual override is only accessed upon entering a password or key code into the computer.

Other objects of the invention are achieved by providing a kit for retrofitting a computer with an external defibrillator, the kit comprising: a slave device, the slave device including a defibrillator element, the defibrillator element having at least one cable and at least one electrode pad, the at least one cable and at least one electrode pad being housed in a compartment in the slave device; and an electronic connector component, the electronic connector component being housed in an additional compartment, the electronic connect component connecting the defibrillator element to the computer, so that the computer controls the defibrillator element during use of the defibrillator element.

In certain embodiments, the adjustable case further comprises a defibrillator control element, the defibrillator control element being housed within a separate compartment in the adjustable case.

In certain embodiments, the defibrillator control element is only accessed upon entering a password or key code into the computer.

In certain embodiments, the defibrillator control compartment includes an external flap that can swing open, allowing the defibrillator control element to be accessed. In certain embodiments, the defibrillator control element within the defibrillator control compartment is in the form of a button, switch, or alternative control.

In certain embodiments, the electrode lead compartment is only accessed by activating the defibrillator control element within the defibrillator control compartment.

In certain embodiments, the at least one cable and at the least one electrode pad are directly attached to the defibrillator element within that compartment.

In certain embodiments, the electronic connector component is selected from a group consisting of a USB cable, a cable wire, port adaptors, a Y-shaped cable, two USB connectors or BLUETOOTH.

As in the adjustable case; in certain embodiments, the slave device further comprises a manual over-ride, the manual over-ride providing the ability to administer a defibrillating shock from the defibrillator element. The manual over-ride allows a medical professional to bypass the automated component of the AED (automated external defibrillator), which when in automated mode proceeds with an analysis of the sudden cardiac arrest victim's heart rhythm. The manual over-ride provides a saving of time for the medical professional who may elect to defibrillate without automated heart rhythm analysis. The manual over-ride allows a medical professional to administer a defibrillating shock from the defibrillator element, even though the proper access code is not entered into the computer. In certain embodiments, the manual override is only accessed upon entering a password or key code into the computer.

In certain embodiments, the slave device includes software to provide an instantaneous connection to the computer. In certain embodiments, the slave device has a height of less than five inches, a length of less than three inches and a width of less than two inches.

Other objects of the invention include a method for employing a slave AED comprising: pressing the USB compartment release button or latch release on the exterior surface of the "slave" AED; gaining access to the USB compartment, and the at least one straight or coiled USB cable; inserting the USB plug on the cable into a USB port of the paired computer device, selected from a group consisting of a notebook, a laptop computer, or a tablet computer; entering the password control into the paired computer; gaining access into a compartment housing the defibrillator control; activating the defibrillator control; gaining access into the electrode lead compartment; following the voice and visual prompts for attaching the electrode leads and pads to the victim, and proceed as instructed.

Other objects of the invention are achieved by providing a portable external defibrillator comprising: a computer; a defibrillator element; and a defibrillator control, the defibrillator control being housed within a compartment in the computer. The defibrillator control may be a button, switch, or other such control that needs to be activated in order to activate the defibrillator element. The compartment may have an external flap or lid that can swing upon, allowing the defibrillator control to be accessed. The compartment may additionally have sufficient depth to allow the defibrillator control to fit within the compartment.

The computer may be a notebook, a laptop computer or a tablet computer. A notebook is defined as a personal computer for mobile use that includes a display, a keyboard, and a pointing device (a touchpad, also known as a trackpad or pointing stick) in a single unit. It is very different than the device that is attached to a wall such as described in U.S. Patent Publication No. 2007/0299473 (Matos).

In certain embodiments of the invention, the portable external defibrillator may have the defibrillator control only accessible by entering a password control into the computer. In certain embodiments of the invention, the password control may be a preset password or may be a general key code. Having a password control helps ensure that unauthorized users do not accidentally trigger the defibrillation capabilities of the device. Additionally, the contents of the defibrillator control compartment of the computer may only be accessed after the password control is entered into the computer. This may be done as the external flap or lid of the defibrillator control compartment will only open after the password control is entered.

In certain embodiments of the invention, the portable external defibrillator may further comprise another compartment, the compartment housing at least one cable and at least one electrode pad. This may also be referred to as the electrode lead compartment. Preferably, two cables and two electrode pads are used, so that an electric shock may be provided to both sides of a victim's chest. Additionally, the compartment may have an external flap or lid that can swing open, allowing the at least one cable and at least one electrode pad to be accessed. Also, the compartment may additionally have sufficient depth to allow the at least one cable and at least one electrode pad to fit comfortably inside the compartment.

In certain embodiments of the invention, the at least one cable and at least one electrode pad are preferably connected and attached to the defibrillator element, either directly or detachably. In certain embodiments the at least one cable and at least one electrode pad are detachable from the defibrillator element to enable replacement upon expiration and/or upon a defect alert, both provided by the retrofitted computer, laptop computer, notebook computer or tablet computer. In certain embodiments of the invention, the defibrillator element may be housed within the body of the computer, laptop, notebook or tablet computer.

In certain embodiments of the invention, the compartment in the computer, laptop, notebook or tablet computer having the cables may only be accessed by activating the defibrillator control. This allows for a sequential and simultaneous control that minimizes the chance of an accidental shock from the defibrillator, and helps ensure that unauthorized users do not accidentally trigger the defibrillation capabilities of the device.

In order to use the portable external defibrillator, the at least one electrode pad must be attached to a person to deliver an electric shock. To use this device, it is preferable that the at least one electrode pad be attached to the skin of the sudden cardiac arrest victim to deliver the shock.

In certain embodiments of the invention, the portable external defibrillator may further comprise an assessment circuit that assesses whether the at least one electrode pad is properly attached to a person. Once properly attached, the assessment circuit can then allow an electric shock to be transmitted if the defibrillator is a fully automated defibrillator.

In instances where the defibrillator is a shock-advisory defibrillator, the portable external defibrillator may further comprise a shock control, the shock control requiring activation to deliver an electric shock. This shock control can be a button or can be a touch screen element where a user may press the shock control to initiate the electric shock.

In certain embodiments of the invention, the portable external defibrillator may further comprise audio voice and visual prompts to guide a user through defibrillation of a person. The audio voice and visual prompts may teach a sequential sequence of steps whereby a person is guided through steps to deliver an electric shock to a victim suffering from VF sudden cardiac arrest.

In certain embodiments of the invention, the portable external defibrillator may provide low energy electric shocks ranging from 120-200 joules. Additionally, the portable external defibrillator may provide either higher or lower energy electric shocks and may provide more than one electric shock to a victim suffering from VF sudden cardiac arrest.

The portable external defibrillator may also have the capability to determine if a person is in ventricular fibrillation. This is an additional safety component to ensure that an electric shock is indeed needed. This is typically done as the portable external defibrillator performs an instantaneous electrocardiogram.

Other objects of the invention are achieved by providing a method for using a portable external defibrillator device, comprising the steps of: entering a preset password into the portable automated external defibrillator device; opening a compartment housing a defibrillator control; pressing the defibrillator control to open a compartment housing at least one cable and at least one electrode pad; applying the at least one electrode pad to a person that requires defibrillation; and initiating an electronic shock to the person, wherein the electric shock is provided by a defibrillator. The electronic shock may be administered to a victim of sudden cardiac arrest using a fully automated defibrillator, a shock-advisory defibrillator or a defibrillator in manual over-ride mode.

The method may further comprise the step of following audio and/or visual prompts so that a user can properly use the portable automated external defibrillator device.

The step of entering a preset password into the portable automated external defibrillator device may simultaneously perform the step of opening a compartment housing a defibrillator control as well as also initiating the step of following audio and/or visual prompts so that a user can properly operate the portable automated external defibrillator device.

The step of initiating an electronic shock to the person may first involve determining if the person is indeed in ventricular fibrillation. The defibrillator used for this method may be either a fully automated defibrillator or a shock-advisory defibrillator. The computer used for this method may be selected from a group consisting of a notebook, a laptop computer, a tablet computer, or an IPad®.

Other objects of the invention are achieved by providing a portable external defibrillator system integrated into a computer, which includes a portable AED (automated external defibrillator) device joined to or connected to a computer; a defibrillator control compartment, the defibrillator control compartment housing a defibrillator control; and an electrode lead compartment, the electrode lead compartment housing a defibrillator element and two cables and two electrode pads, the two cables being connected to the defibrillator element, wherein the defibrillator control can only be accessed by entering a password control into the computer, and wherein the electrode lead compartment can only be accessed by activating the defibrillator control. The two cables may be detachable and may be directly connected to the defibrillator element in certain embodiments.

The terms "first compartment" and "second compartment" refer to separate compartments providing the defibrillator control element in one compartment and the at least one cable and at least one electrode pad in the other compartment. The terms "first compartment" and "second compartment" may also be referred to as "compartment", "another compartment" or "additional compartment."

Other objects of the invention are achieved by providing a portable external defibrillator system integrated into a computer comprising: a computer selected from a group consisting of a notebook, a laptop computer, a tablet computer, or a desktop computer, wherein the notebook and the laptop computer each include a display, a keyboard and a pointing device. The computer may be encompassed by, held by, or surrounded by and is attached to, or may simply be joined or attached to, a portable AED device or kit comprising a defibrillator element, wherein the defibrillator element provides low energy shocks of 120-200 joules; a defibrillator control, the defibrillator control being housed within a defibrillator control compartment in the portable AED device or kit; and a electrode lead compartment, the electrode lead compartment housing at least one cable and at least one electrode pad.

Other objects of the invention and its particular features and advantages will become more apparent from consideration of the following drawings and accompanying detailed description. It should be understood that the detailed description and specific examples, while indicating the preferred embodiment of the invention, are intended for purposes of illustration only and are not intended to limit the scope of the invention.

DETAILED DESCRIPTION OF THE INVENTION

Figure 1:
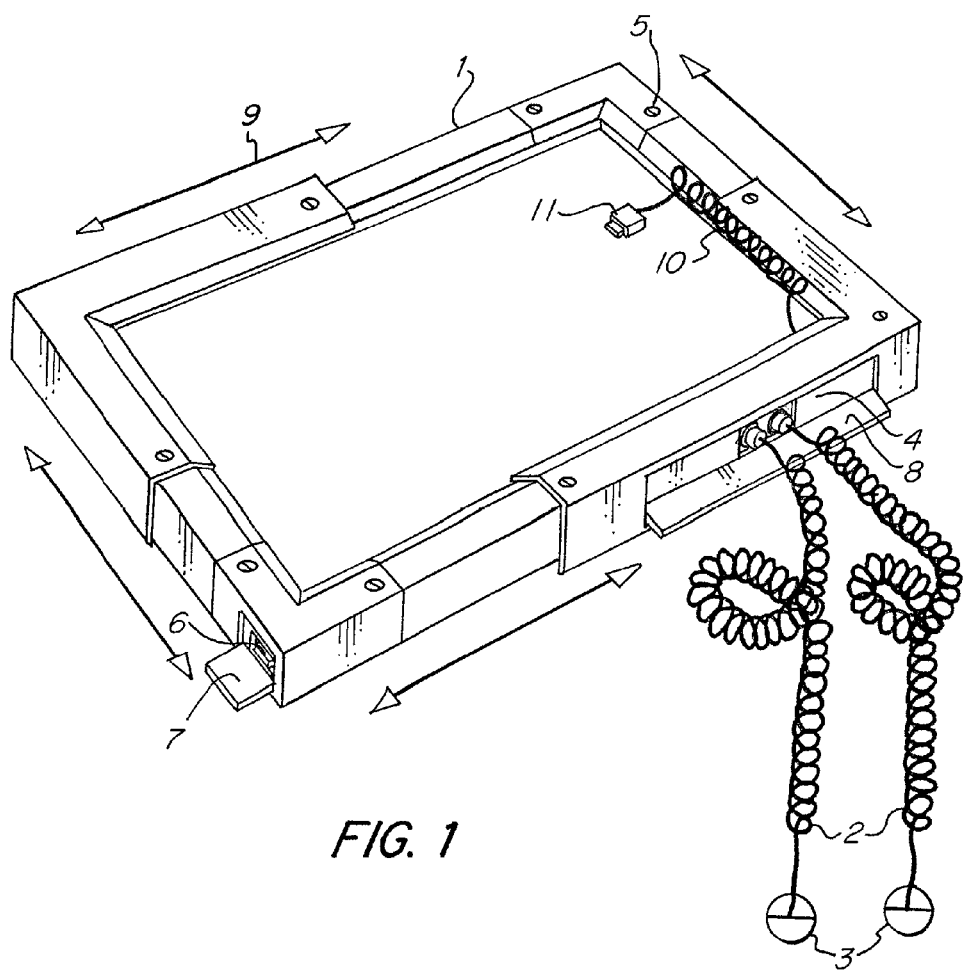
FIG. 1 is a perspective view of a kit in the form of an adjustable universal case, receptacle, holder or frame integrated with an automated external defibrillator (AED) in one embodiment of the present invention.
Figure 2:
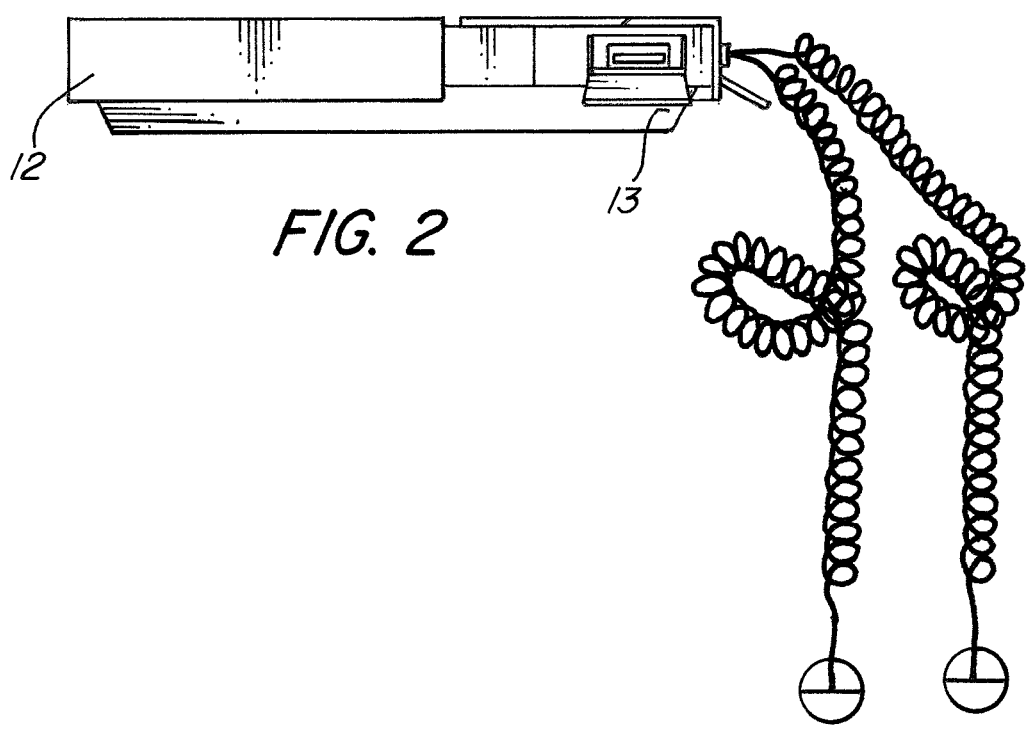
FIG. 2 is a side view of the proposed kit of FIG. 1 in the form of an adjustable universal case, receptacle, holder or frame; showing an automated external defibrillator (AED) in one embodiment of the present invention, within the adjustable compartment comprising the posterior surface of the case, receptacle, holder or frame.

The present disclosure proposes incorporating a modified form of current portable Automated External Defibrillator technology into a computer, notebook, laptop computer or tablet computer (such as an iPad®). Additionally, the present invention also relates to certain methods and apparatuses for implementing the common notebook, laptop computer and tablet computer as an AED.

Newer AEDs (manufactured after late 2003) have tended to utilize biphasic algorithms which give two sequential lower-energy shocks of 120-200 joules, with each shock moving in an opposite polarity between the pads. This lower-energy waveform has proven more effective in clinical tests, and offers a reduced rate of complications and recovery time.

The present disclosure proposes that this biphasic waveform technology be incorporated into the common notebook, laptop computer and tablet computer. It is designed to be simple enough for those with minimal training to use.

In certain embodiments of the invention, a kit is provided in the form of an adjustable universal case, receptacle, holder or frame with an integrated automated external defibrillator for receiving, encompassing and adapting a common notebook, laptop computer or tablet computer to convert and enable each to be used as an automated external defibrillator (AED).

Other embodiments of the invention provide a kit, in the form of a "slave" automated external defibrillator (AED) that is joined to a common notebook, laptop computer, or tablet computer, to adapt, convert, and enable each, the common notebook, laptop computer, and tablet computer to be used as an automated external defibrillator (AED). Such embodiments provide methods utilizing AED devices, for adapting and converting the millions of after-market common notebooks, laptop computers, and tablet computers, already in use globally, as well as those currently being manufactured and marketed.

In certain embodiments of the invention, the leads or cables and electrode pads are directly attached to a defibrillator element within the adjustable universal case, receptacle, holder or frame, so that leads or cables and electrode pads need not be connected to the defibrillator element at the time a victim is suffering from VF cardiac arrest, saving time which is vital to improve the chances of survival of the victim. In certain embodiments the leads or cables and electrode pads are connected, but detachable from the defibrillator element within the adjustable case, to enable replacement upon expiration and/or upon a defect alert, both provided by the retrofitted computer, laptop computer, notebook computer or tablet computer. These latter embodiments also avoid the need for the leads or cables and electrode pads to be connected to the defibrillator element at the time a victim is suffering from VF cardiac arrest, saving time which is vital to improve the chances of survival of the victim.

In certain embodiments of the invention, the reduced scale leads or cables (straight or coiled) and electrode pads are housed within a compartment of the kit.

In certain embodiments of the invention, the defibrillator control is housed within a separate compartment of the kit, such as the adjustable universal case, receptacle, holder or frame. In certain embodiments, the defibrillator control may be a button, switch, or other such control that needs to be activated in order to activate the defibrillator element. The compartment may have an external flap or lid that can swing open, allowing the defibrillator control to be accessed. The compartment may additionally have sufficient depth to allow the defibrillator control to fit within the compartment.

In certain embodiments of the invention, the defibrillator control is only accessed upon entering a password or key code into the common notebook, laptop computer, tablet computer, thus, improving the safety of the device, whereby accidental use of the defibrillator element is minimized, if not eliminated. The password control may be a preset password or may be a general key code. Having a password control helps ensure that unauthorized users do not accidentally trigger the defibrillation capabilities of the device. Additionally, the contents of the defibrillator control compartment of the adjustable universal case, receptacle, holder or frame may only be accessed after the password control is entered into the computer. This may be done as the external flap or lid of the defibrillator control compartment will only open after the password control is entered.

In certain embodiments of the invention, the adjustable universal case, receptacle, holder or frame is integrated with an automated external defibrillator (AED). The AED is accessed with the common notebook, laptop computer, or tablet computer through at least one straight or coiled USB cable and plug from the automated external defibrillator (AED) integrated within the adjustable universal case, receptacle, holder or frame to a USB port (receptacle) of the common notebook, laptop computer, or tablet computer encompassed, held and contained therein.

In certain embodiments of the invention, one or more alternate connection systems (other than standard USB connection systems) may be implemented for accessing the adjustable universal case, receptacle, holder or frame integrated with an automated external defibrillator (AED) to its contained common notebook, laptop computer, or tablet computer; and various required accessories may be implemented, such as plug and/or port (receptacle) adaptors, an external power source, or additional USB cables and connections, or a Y-shaped cable that has two USB connectors (one for power+ data, the other for power only) to be plugged into a computer. With such cables, a device can draw power from two USB ports simultaneously.

In certain embodiments of the invention, a method is provided for using a portable external defibrillator device integrated within the kit in the form of an adjustable universal case, receptacle, holder or frame, and having steps for accessing the defibrillator control located within a compartment in the adjustable universal case, receptacle, holder or frame, as well as accessing an electrode lead compartment housing at least one straight or coiled lead or cable, and at least one electrode pad and applying that electrode pad to a person that requires defibrillation. This is an example of a two-step or sequential step control process.

In certain embodiments of the invention, a method for enabling or activating a portable automated external defibrillator device is provided, the device being enabled or activated by insertion of a final chip upon having a user complete a training program to learn the proper administration of quality CPR and the approved technique for using an automated external defibrillator (AED). This allows for maximizing the safety of an operator using a defibrillator as well as the safety of a victim suffering from sudden cardiac arrest.

Referring to FIG. 1, an adjustable universal case, receptacle, holder or frame is integrated with an automated external defibrillator (AED), and houses reduced scale leads or cables (straight or coiled) and electrode pads within a compartment enclosed within the adjustable universal case, receptacle, or holder. The adjustable case is in the form of a frame with four L-shaped members. In FIG. 1, the four L-shaped members are configured to telescope over and under each other or into and out of each other to thereby adjust the length and width of the device, thereby enabling the holder to accommodate and encompass a common notebook, laptop computer, or tablet computer, of various dimensions and to enable each to be used as an AED.

In the above embodiment, the depth dimension (9) (See FIG. 1) is adjustable by providing similar members that would either telescope over and under or telescope into and out of each other to thereby adjust the depth of the device, and thereby enable the adjustable universal case, receptacle, or holder to accommodate, encompass and hold a common notebook, laptop computer, or tablet computer, of various depth dimensions.

The length, width and depth of the case, receptacle, holder or frame (1) integrated with an automated external defibrillator, and which houses reduced scale leads or cables (straight or coiled) (2) and electrode pads (3) within a compartment (4) enclosed within the adjustable universal case, receptacle, or holder (1) is readily adjustable by loosening the appropriate thumb screw(s) or thumb-turn(s) (5), adjusting the length, width and depth to accommodate and hold a common notebook, laptop computer, or tablet computer, of various dimensions, then retightening the thumb screw(s) or thumb-turn(s). Alternatives to the thumb screws or thumb-turns would be a locking mechanism or friction mechanism for holding the common notebook, laptop computer, or tablet computer, of various dimensions in place.

In the above embodiment, the posterior area within the frame dimensions could either be open, or could be comprised of a surface with an ability to change dimensions consistent with the adjustable length and width dimensions of the surrounding frame. This would be readily accomplished by providing an adjustable border to the posterior surface comprising the capability to change length and width dimensions by providing members to the border that either telescope over and under or into and out of each other to thereby adjust to changes in the surrounding frame dimensions and thereby enabling the holder to accommodate and hold a common notebook, laptop computer, or tablet computer, of various dimensions.

In certain embodiments, the defibrillator element is housed or encompassed within the frame of the proposed device.

The portable automated external defibrillator may have the defibrillator control only accessible by entering a password control into the computer. The password control may be a preset password or may be a general key code. Having a password control helps ensure that unauthorized users do not accidentally trigger the defibrillation capabilities of the device. Additionally, the contents of the defibrillator control compartment (6) of the adjustable universal case, receptacle, holder or frame may only be accessed after the password control is entered into the computer. This may be done as the external flap or lid (7) of the defibrillator control compartment will only open after the password control is entered.

Another embodiment of the present invention would be a proposed kit in the form of an adjustable universal case, receptacle, holder or frame integrated with an automated external defibrillator (AED), and housing in an electrode lead compartment (4) at least one reduced scale lead or cable and at least one electrode pad. Preferably, two reduced scale leads or cables (straight or coiled) (2), and two electrode pads (3) are used, so that an electric shock may be provided to both sides of a victim's chest. Additionally, the compartment may have an external flap or lid (8) that can swing open, allowing the at least one cable and at least one electrode pad to be accessed. Also, the compartment (4) may additionally have sufficient depth to allow the at least one lead or cable and at least one electrode pad to fit readily inside the compartment which houses the leads or cables and electrode pads within the adjustable universal case, receptacle, holder or frame. The Kit in the form of an adjustable universal case, receptacle, holder or frame is in the form of a frame with 4 L-shaped members in which the automated external defibrillator (AED) would be integrated in a compartment comprising the posterior surface of the case, receptacle, holder or frame; and with reduced scale leads or cables (straight or coiled) and electrode pads either within the adjustable compartment comprising the posterior surface of the case, receptacle, holder or frame, or within a compartment, as shown, in the adjustable frame of the universal case, receptacle or holder.

This electrode lead compartment (4) within the adjustable universal case, receptacle, holder or frame may only be accessed by activating the defibrillator control (6). This allows for a sequential and simultaneous control that minimizes the chance of an accidental shock from the defibrillator, and helps ensure that unauthorized users do not accidentally trigger the defibrillation capabilities of the device.

In certain embodiments of the invention, the leads or cables (2) and electrode pads (3) may be directly attached to a defibrillator element within the adjustable universal case, receptacle, holder or frame, so that cables and electrode pads need not be connected to the defibrillator element at the time that a victim is experiencing VF sudden cardiac arrest, saving time which is vital to improve the chances of survival of the victim. In certain embodiments the leads or cables and electrode pads are connected, but detachable from the defibrillator element within the adjustable case, to enable replacement upon expiration and/or upon a defect alert, both provided by the retrofitted computer, laptop computer, notebook computer or tablet computer.

In order to use the portable external defibrillator, the at least one electrode pad must be attached to a person to deliver an electric shock. To use this device, it is preferable that the at least one electrode pad be attached to the skin of the person receiving the shock.

The portable external defibrillator may further comprise an assessment circuit that assesses whether the at least one electrode pad is properly attached to a person. Once properly attached, the assessment circuit can then allow an electric shock to be transmitted if the defibrillator is a fully automated defibrillator.

In instances where the defibrillator is a shock-advisory defibrillator, the portable external defibrillator may further comprise a shock control, the shock control requiring activation to deliver an electric shock. This shock control can be a button or can be a touch screen element where a user may press the shock control to initiate the electric shock.

In certain embodiments of the invention, the kit has the capability of an optional manual over-ride, affording a healthcare provider (physician, nurse, advanced EMT, paramedic, and the like) the ability to administer a defibrillating shock at his or her discretion. It is a further object of the present invention for access to this option of the defibrillator control, to be regulated or controlled by entering a specific manual over-ride preset password or a specific key code, to limit access of this option to only medical professionals, as described.

The portable external defibrillator may further comprise voice and visual prompts to guide a user through defibrillation of a person. The voice and visual prompts may teach a sequential sequence of steps whereby a person is guided through steps to deliver an electric shock to a victim suffering from VF sudden cardiac arrest.

The portable external defibrillator may provide low energy electric shocks ranging from 120-200 joules. Additionally, the portable external defibrillator may provide either higher or lower energy electric shocks and may provide more than one electric shock to a victim suffering from VF sudden cardiac arrest.

The portable external defibrillator may also be capable of determining if a person is in ventricular fibrillation. This is an additional safety component to ensure that an electric shock is indeed needed. This is typically done as the portable external defibrillator performs an instantaneous electrocardiogram.

Other objectives of the invention are achieved by providing a method for using a portable automated external defibrillator device integrated within the adjustable universal case, receptacle, holder or frame, comprising the steps of: entering a preset password into the portable automated external defibrillator device; opening a defibrillator control compartment housing a defibrillator control (6); pressing the defibrillator control to open an electrode lead compartment (4) housing at least one cable and at least one electrode pad; applying the at least one electrode pad to a person that requires defibrillation; and initiating an electronic shock to the person, wherein the electric shock is provided by a defibrillator.

The method may further comprise the step of following voice and/or visual prompts so that a user can properly use the portable automated external defibrillator device integrated within the adjustable universal case, receptacle, holder or frame.

The step of entering a preset password into the portable automated external defibrillator device integrated within the adjustable universal case, receptacle, holder or frame may simultaneously perform the step of opening a defibrillator control compartment housing a defibrillator control, as well as also initiating the step of following voice and/or visual prompts so that a user can properly use the portable automated external defibrillator device integrated within the adjustable universal case, receptacle, holder or frame.

The step of initiating an electronic shock to the person may first involve determining if the person is indeed in ventricular fibrillation. The defibrillator used for this method may be either a fully automated defibrillator or a shock-advisory defibrillator, or a defibrillator with a manual over-ride. The computer used for this method may be selected from a group consisting of a notebook, a laptop computer, or a tablet computer.

It is a further object of an embodiment of the present invention, for the adjustable universal case, receptacle, holder or frame integrated with an automated external defibrillator (AED) to access its contained common notebook, laptop computer, or tablet computer through at least one USB cable (10) and plug (11) from the automated external defibrillator (AED) integrated adjustable universal case, receptacle, holder or frame to the USB port (receptacle) of the common notebook, laptop computer, or tablet computer contained, held or encompassed therein.

And, as noted earlier, it is a further object of the present invention, that one or more alternate connection systems (other than standard USB connection systems) may be implemented for accessing the adjustable universal case, receptacle, holder or frame integrated with an automated external defibrillator (AED) to its contained common notebook, laptop computer, or tablet computer; and various required accessories may be implemented, such as plug and/or port (receptacle) adaptors, an external power source, or additional USB cables and connections, or a Y-shaped cable that has two USB connectors (one for power+data, the other for power only) to be plugged into a computer. With such cables, a device can draw power from two USB ports simultaneously.

Other objectives of the invention are achieved by providing a method for activation of a portable automated external defibrillator (AED) device integrated in an adjustable universal case, receptacle, holder or frame comprising the steps of: providing a portable external defibrillator, the portable external defibrillator being unenabled; participating in a training program of how to use the portable external defibrillator; taking the portable automated external defibrillator to an activation or service center upon completion of the training program; and placing a final chip within the portable automated external defibrillator, said final chip enabling the defibrillation function of the portable automated external defibrillator (AED) integrated within an adjustable universal case, receptacle, holder or frame. The training program may be a certified training program. Additionally, the training program may involve an online or web tutorial in place of, or in addition to the certified training program.

The method may further comprise the step of receiving a certificate upon completing the training program of how to use the portable automated external defibrillator (AED) integrated in an adjustable universal case, receptacle, holder or frame, and showing the certificate to a person at the activation or service center to prove the training program was successfully completed. Once the training program is completed and the certificate is shown, the final chip enabling the defibrillator function of the portable automated external defibrillator (AED) integrated in an adjustable universal case, receptacle, holder or frame is placed within the device. This allows for increased safety as only persons that complete the training program successfully will be able to have their portable automated external defibrillator (AED) integrated in an adjustable universal case, receptacle, holder or frame capable of emitting an electric shock. Devices that do not have this final chip will not be able to perform the defibrillator function.

Figure 3:
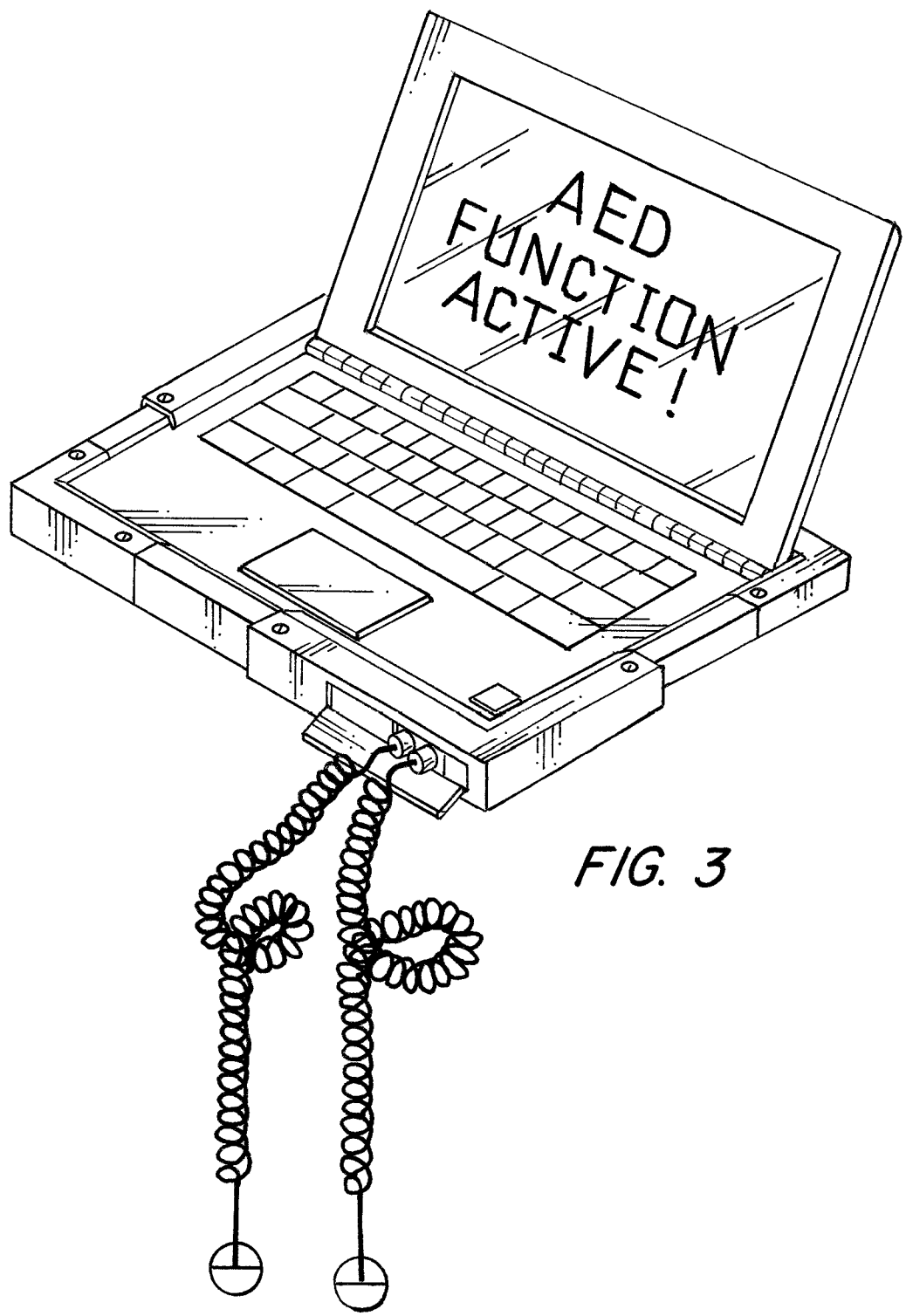
FIG. 3 is an perspective view of a notebook or laptop computer contained, held or encompassed within the kit of FIG. 1, which is shown with the AED function activated.
Figure 4:
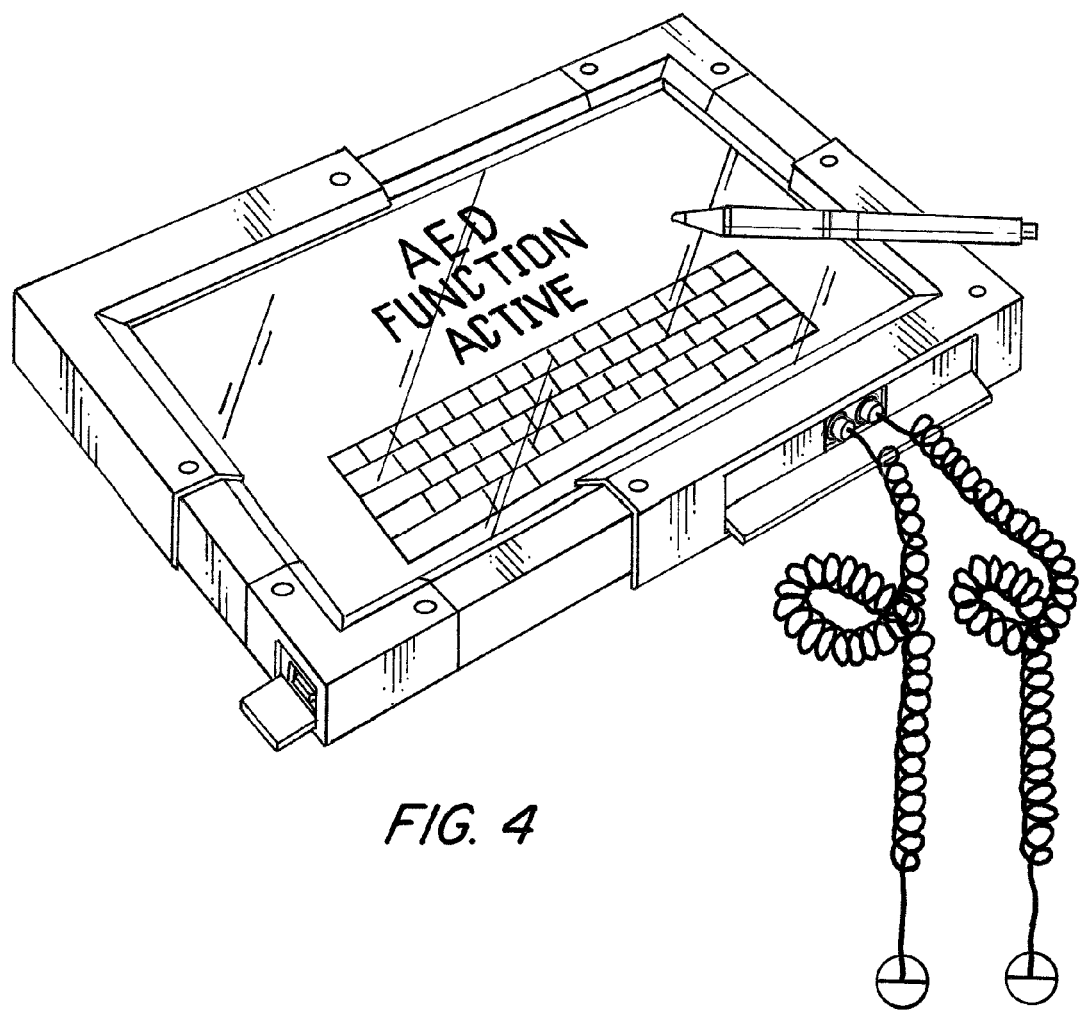
FIG. 4 is a perspective view of a tablet computer contained, held or encompassed within the kit of FIG. 1, which is shown with the AED function activated with keyboard and writing capabilities evident.

It is a further object of the present invention, for the adjustable universal case, receptacle, holder or frame integrated with an automated external defibrillator (AED), to be capable of receiving, encompassing, containing, holding and adapting a common notebook computer, a laptop computer (See FIG. 3) or a tablet computer (See FIG. 4) of all dimensions, to adapt, convert, and enable each to be used as an automated external defibrillator (AED). The common notebook computer, laptop computer and tablet computer sizes may range considerably; from the large rugged laptops and tablet computers used in the field; such as by first responders, the military, and in government, industry and construction, to mid-sized common notebook computers, laptop computers and tablet computers, and to ultra-small and ultra-thin common notebook computers, laptop computers and tablet computers. Accordingly, it is a further object of the present invention to propose that for each of these size groups the adjustable universal case, receptacle, holder or frame integrated with an automated external defibrillator (AED) be capable of receiving, encompassing, containing or holding a common notebook computer, a laptop computer or a tablet computer, of at least one or more sizes, to accommodate all of the computers within the size groups, so described.

Other objectives of the invention are achieved by providing a portable external defibrillator (AED) system integrated into an adjustable universal case, receptacle, holder or frame comprising; a defibrillator control compartment, the defibrillator control compartment housing a defibrillator control; and an electrode lead compartment, the electrode lead compartment housing a defibrillator element and reduced scale leads or cables (straight or coiled) and electrode pads; the two leads or cables being connected to the defibrillator element, wherein the defibrillator control can only be accessed by entering a password control into the computer, and wherein the electrode lead compartment can only be accessed by activating the defibrillator control. In certain embodiments, the leads are detachable leads. In certain embodiments, the cables are directly connected to the defibrillator element.

Figure 5:
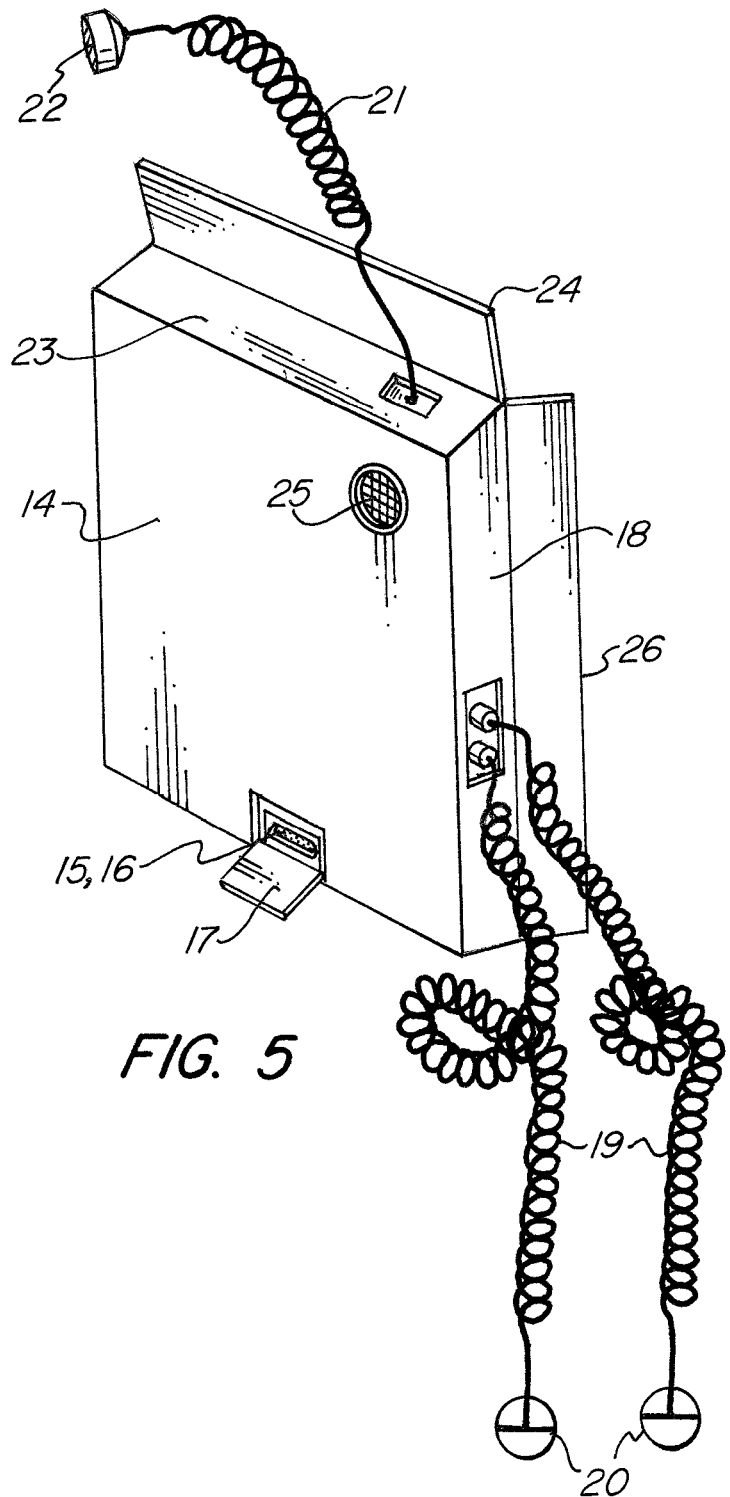
FIG. 5 is a perspective view of another embodiment of the present invention showing a kit in the form of a "slave" AED, capable of joining to a common notebook, laptop computer, or tablet computer.

Another embodiment of the present invention would be the joining of a "slave" automated external defibrillator (AED) (see FIG. 5), to a common notebook, laptop computer, or tablet computer, to adapt, convert, and enable each, the common notebook, laptop computer, or tablet computer to be used as an automated external defibrillator (AED). The term "slave" as used here, defined in the Merriam Webster Dictionary as "a device (as the printer of a computer) that is directly responsive to another"; accordingly, this definition applies to both of the devices described in the instant invention: 1) in the form of the proposed adjustable universal case, receptacle, holder or frame integrated with an automated external defibrillator (AED); and 2) in the form of a proposed "slave" automated external defibrillator (AED). The dimensions and weight of the "slave" automated external defibrillator (AED) (14) is approximate to those of a standard deck of cards, or less; and readily fits into a pocket, to be carried by physicians, nurses and staff members in offices and hospitals, first responders, members of the military, various members of government and industry, and members of the general public.

The diminutive size and weight of the "slave" AED is made possible by isolating the usual AED hardware elements of existing automated external defibrillators; less the case, LCD screen, and all elements, microprocessors, software and functions that can be readily assumed by the paired common notebook, laptop computer, or tablet computer. The remaining critical defibrillator hardware elements can be readily incorporated into the body of the proposed "slave" automated external defibrillator (AED), as described herein.

In certain embodiments of the invention, the kit in the form of the proposed "slave" automated external defibrillator (AED) comprises the capability of an optional manual over-ride, affording a healthcare provider (physician, nurse, advanced EMT, paramedic, and the like), the ability to administer a defibrillating shock at his or her discretion. It is a further object of the present invention for access to this option of the defibrillator control, to be regulated or controlled by entering a specific manual over-ride preset password or a specific key code, to limit access of this option to only medical professionals, as described.

It is a further objective of the present invention that all of the above proposed objectives pertaining to the portable automated external defibrillator (AED) system integrated into a kit in the form of an adjustable universal case, receptacle, holder or frame be applied to this "slave" embodiment of the present invention as well, to include comprising; a defibrillator control compartment (15), the defibrillator control compartment housing a defibrillator control (16), which would only be accessed upon entering a password or key code into the common notebook, laptop computer, tablet computer; thus, improving the safety of the device, and whereby accidental use of the defibrillator element is minimized, if not eliminated. The compartment may have an external flap or lid (17) that can swing open, allowing the defibrillator control to be accessed. The compartment may additionally have sufficient depth to allow the defibrillator control to fit within the compartment. The "slave" automated external defibrillator (AED) would comprise an electrode lead compartment (18), the electrode lead compartment housing a defibrillator element and reduced scale leads or cables (straight or coiled) (19) and electrode pads (20) within the compartment in the "slave" AED. The electrode lead compartment is only accessed by activating the defibrillator control within the defibrillator control compartment, in the form of a button, switch, or alternative control. This is an example of a two-step or sequential step control process. It is another object of the present invention for the reduced scale leads or cables (straight or coiled) and electrode pads to be connected or detachably attached to a defibrillator element within the "slave" automated external defibrillator (AED), so that leads or cables and electrode pads need not be connected to the defibrillator element at the time a victim is suffering from VF cardiac arrest, saving time which is vital to improve the chances of survival of the victim.

It is a further object of the present invention, for the integrated "slave" automated external defibrillator (AED) to access its paired common notebook, laptop computer, or tablet computer through at least one straight or coiled USB cable (21) and plug (22) from the automated external defibrillator (AED) integrated within the "slave" device (14) to a USB port of the paired common notebook, laptop computer, or tablet computer. The straight or coiled USB cable (21) and plug (22) from the automated external defibrillator (AED) integrated within the "slave" device is accessed within an additional compartment (23) of the "slave" AED (14), the lid (24) of which opens upon pressing a recessed release button or latch release (25) on the exterior surface of the device, thereby enabling USB access of the "slave" AED to its paired common notebook, laptop computer, or tablet computer. Opening the lid (17) of the defibrillator control compartment (15), can only be accomplished by entering a password control into the paired computer, and wherein opening the lid (26) to the electrode lead compartment (18) can only be accomplished by activating the defibrillator control (16) within the defibrillator control compartment (15).

Therefore, the step sequence for employing the 'slave' AED would be as follows: 1) press the USB compartment release button or latch release (25) on the exterior surface of the "slave" AED; 2) having gained access to the USB compartment (23), and the at least one straight or coiled USB cable (21); 3) insert the USB plug (22) on the cable into a USB port of the paired computer device, selected from a group consisting of a notebook, a laptop computer, or a tablet computer; 4) enter the password control into the paired computer; 5) having gained access into the defibrillator control compartment (15), housing the defibrillator control (16), activate the defibrillator control (16); 6) having gained access into the electrode lead compartment (18); 7) follow the voice and visual prompts for attaching the electrode leads (19) and pads (20) to the victim, and proceed as instructed.

It is a further object of the present invention, that one or more alternate connection systems (other than standard USB connection systems) may be implemented for accessing the "slave" automated external defibrillator (AED) to its paired common notebook, laptop computer, or tablet computer; and various required accessories may be implemented, such as plug and/or port (receptacle) adaptors, an external power source, or additional USB cables and connections, or a Y-shaped cable that has two USB connectors (one for power+ data, the other for power only) to be plugged into a computer. With such cables, a device can draw power from two USB ports simultaneously.

It is a further object of the present invention, for the kit in the form of a "slave" automated external defibrillator (AED), It is a further object of the present invention for both of the proposed kits: 1) in the form of the proposed adjustable universal case, receptacle, holder or frame integrated with an automated external defibrillator (AED); and 2) in the form of a proposed "slave" automated external defibrillator (AED).

It is a further object of the present invention, for the kit to possess the necessary implementing software, available for instant transfer to the paired common notebook, laptop computer, or tablet computer upon accessing the "slave" automated external defibrillator (AED) to its paired common notebook, laptop computer, or tablet computer through at least one straight or coiled USB cable (21) and plug (22) from the automated external defibrillator (AED) integrated within the "slave" device (14), to a USB port (receptacle) of the paired common notebook, laptop computer, or tablet computer; and, to thus provide instantaneous enabling of any and all common notebooks, laptop computers, or tablet computers as an automated external defibrillator (AED).

It is a further object of the present invention for both of the proposed kits: 1) in the form of the proposed adjustable universal case, receptacle, holder or frame integrated with an automated external defibrillator (AED); and 2) in the form of a proposed "slave" automated external defibrillator (AED), to comprise the capability of being used for both adult and pediatric victims of sudden cardiac arrest (SCA); therefore, necessitating the capability of changing the configurable adult and pediatric energy settings, according to standard values, as the situation requires. The present invention proposes at least two methods for changing the configurable adult and pediatric energy settings, according to standard values, as the situation requires; the first an active method, the second, a passive method.

Accordingly, the present invention proposes the following active and passive methods for changing the configurable adult and pediatric energy settings:

Active method: Early in the voice and visual prompts, a command would be made to enter into a notebook, a laptop computer, or a tablet computer, a choice of either "A" for adult or "P" for pediatric. This prompt would then be repeated for confirmation; thereby, automatically activating the pediatric dose-attenuator system, selecting the clinically appropriate AED defibrillation output. An alternative active method would be a prompt indicating a required choice (in order to proceed) for adult or pediatric, as indicated by pressing a button, moving a switch, lever, dial or alternative indicator to activate the pediatric dose-attenuator system, to select the clinically appropriate AED defibrillation output.

Figure 6:
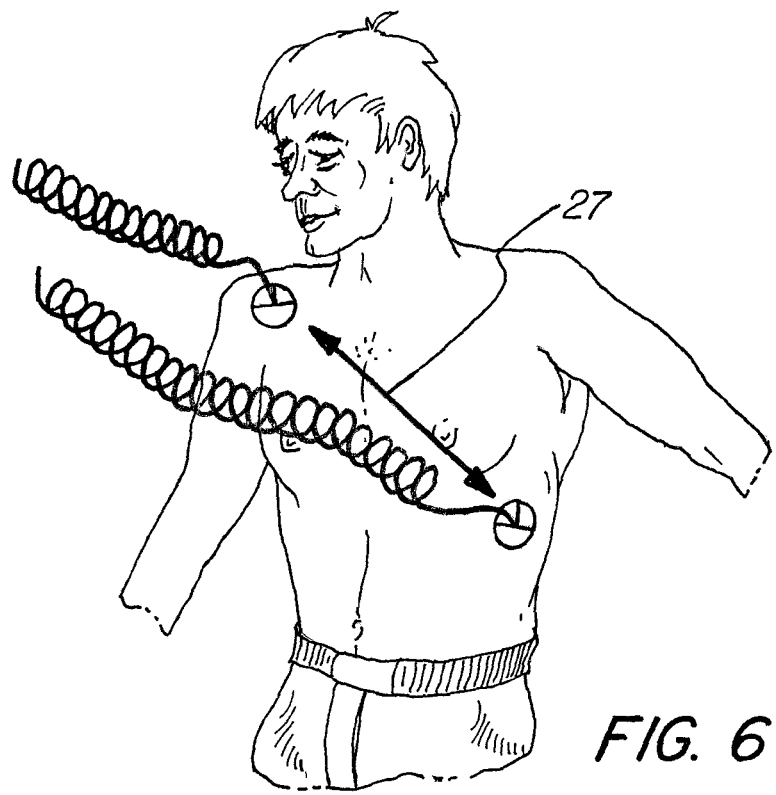
FIG. 6 is an perspective view of the anterior/lateral electrode pad placement.
Figure 7:
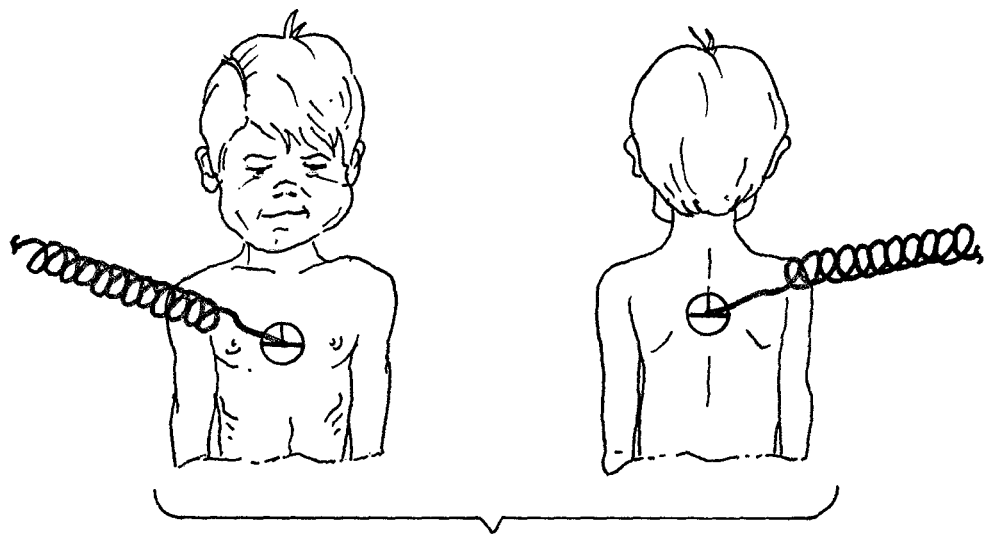
FIG. 7 is an anterior and posterior view of the preferred anterior/posterior pediatric electrode pad placement, for children age eight (8) or less.

Passive method: Research has found that the best pediatric pad placement is achieved utilizing an anterior/posterior placement (one pad on the chest and the other on the back) for infants and children with very small torsos, (See FIG. 7). This method of placement prevents overlap which could lead to arcing. The placement of the electrode pads in an anterior/posterior placement would identify the connection to a pediatric victim; and thereby activate the pediatric dose-attenuator system, selecting the clinically appropriate AED defibrillation output. However, it is still acceptable to use conventional pad placement (anterior/anterior or anterior/lateral) as used in adults (See FIG. 6), when needed in children. The distance between the anterior right chest pad and the anterior (or lateral) left chest pad placements (27), based on preprogrammed pediatric and adult chest dimension values, would identify the connection to a pediatric victim; and thereby activate the pediatric dose-attenuator system, selecting the clinically appropriate AED defibrillation output.

Citing from the 2010 American Heart Association Guidelines for Cardiopulmonary Resuscitation and Emergency Cardiovascular Care Science:

"Data demonstrate that 4 pad positions (anterolateral, anteroposterior, anterior-left infrascapular, and anterior-right-infrascapular) are equally effective to treat atrial or ventricular arrhythmias. There are no studies directly pertaining to placement of pads/paddles for defibrillation success with the end point of ROSC (Return of spontaneous circulation). All 4 positions are equally effective in shock success. Any of the 4 pad positions is reasonable for defibrillation (Class IIa, LOE B). For ease of placement and education, anterolateral is a reasonable default electrode placement (Class IIa, LOE C). Alternative pad positions may be considered based on individual patient characteristics."

"For attempted defibrillation of children 1 to 8 years of age with an AED, the rescuer should use a pediatric dose-attenuator system if one is available. If the rescuer provides CPR to a child in cardiac arrest and does not have an AED with a pediatric dose-attenuator system, the rescuer should use a standard AED. For infants (<1 year of age), a manual defibrillator is preferred. If a manual defibrillator is not available, an AED with pediatric dose attenuation is desirable. If neither is available, an AED without a dose attenuator may be used. Summary: Adult AEDs may be used in all infants and children if there is no child-specific alternative."

In certain embodiments, the AED is for both for adult and pediatric uses. In certain embodiments, there is a retrofit that allows the AED to be used for children and a separate retrofit that allows the AED to be used on adults.

In certain embodiments, upon the charging of the computer, selected from a group consisting of a notebook computer, a laptop computer or a tablet computer; the simultaneous charging of the battery in the connected portable AED (automated external defibrillator) device would take place; this connected portable AED (automated external defibrillator) device includes a portable AED (automated external defibrillator) device integrated in an adjustable universal case, receptacle, holder or frame receiving, encompassing, adapting and converting a common notebook, laptop computer or tablet computer to enable each to be used as an AED, and a portable AED (automated external defibrillator) device integrated in a "slave" AED that is joined to a common notebook, laptop computer or tablet computer to adapt, convert and enable each to be used as an AED. The simultaneous charging of the portable AED (automated external defibrillator) device would ensure the constant readiness and immediate availability of the device for any emergency requiring an AED (automated external defibrillator.

Additionally, in certain embodiments during the simultaneous charging of the portable AED (automated external defibrillator) device so described, there would take place a simultaneous review check and confirmation of the proper functional capability of the AED function of the portable AED (automated external defibrillator) device; to include the functional capacity of the leads or cables and electrode pads. This again, would ensure the constant readiness and immediate availability of the device for any emergency requiring an AED (automated external defibrillator).

Additionally, in certain embodiments, brief periodic electronic voice and visual review tutorials covering the basic techniques of the proper administration of quality CPR and the approved technique for using an automated external defibrillator (AED) with updates, would appear on a computer, notebook or laptop computer, or tablet computer encompassed by, held by or enclosed by and connected to or joined to an adjustable universal case, receptacle, holder or frame with an integrated AED. Similarly, in certain embodiments, brief periodic electronic voice and visual review tutorials covering the basic techniques of the proper administration of quality CPR and the approved technique for using an automated external defibrillator (AED) with updates, would appear on a computer, notebook or laptop computer, or tablet computer connected to or joined to a "slave" AED (automated external defibrillator. It is a further object of embodiments of the present invention, for these brief periodic electronic voice and visual review tutorials to be signaled by an alert sound, on perhaps a monthly or bimonthly basis, confirming proper functional capability of the AED function of the notebook or laptop computer, or tablet computer system connected to or joined to the portable AED (automated external defibrillator) devices so described. This would occur in similar fashion to the periodic NOA Alerts, appearing weekly on all television channels to confirm proper functioning of the NOA Alert Systems.

While the invention has been specifically described in connection with certain specific embodiments thereof, it is to be understood that this is by way of illustration and not of limitation and that various changes and modifications in form and details can be made thereto, and the scope of the appended claims should be construed as broadly as the prior art will permit.

The description of the invention is merely exemplary in nature, and thus, variations that do not depart from the gist of the invention are intended to be within the scope of the invention. Such variations are not to be regarded as a departure from the spirit and scope of the invention.

What is claimed is:

1. A kit configured to retrofit a common computer with an external defibrillator, the kit comprising:
   a device responsive to the retrofitted computer, the responsive device including a defibrillator element, the defibrillator element having at least two cables and at least two electrode pads, the at least two cables and at least two electrode pads being housed in a compartment in the responsive device; and
   an electronic connector component, the electronic connector component connecting the defibrillator element to the retrofitted computer, so that the retrofitted computer controls the defibrillator element during use of the defibrillator element; and
   a defibrillator control element, the defibrillator control element being housed within a separate compartment in the responsive device.
   wherein the retrofitted computer consists of a tablet, a laptop or a notebook.

2. The kit of claim 1, wherein the responsive device has a height of less than five inches, a length of less than three inches and a width of less than two inches.

3. The kit of claim 1, wherein the defibrillator element provides energy shocks that are greater than 200 joules or less than 120 joules.

4. The kit of claim 1, wherein the responsive device includes implementing software for electronically accessing the retrofitted computer.

5. The kit of claim 1, wherein the responsive device includes a power source for powering the defibrillator element.

6. The kit of claim 5, wherein the power source is simultaneously charged with the retrofitted computer.

7. The kit of claim 6, wherein the responsive device includes software that conducts a review check when the power source is simultaneously being charged with the retrofitted computer.

8. The kit of claim 7, wherein the software that conducts the review check occurs on a periodic basis and produces an alert sound to indicate that the review check is occurring.

9. The kit of claim 1, wherein the defibrillator control element is only accessed upon entering a password or key code into the retrofitted computer.

10. The kit of claim 1, wherein the separate compartment includes an external flap that can swing open, allowing the defibrillator control element to be accessed.

11. The kit of claim 1, wherein the compartment is only accessed by activating the defibrillator control element within the separate compartment in the responsive device.

12. The kit of claim 1, wherein the defibrillator control element within the separate compartment is in the form of a button, switch, or alternative control.

13. The kit of claim 1, wherein the at least two cables and the at least two electrode pads are directly connected to or detachably connected to the defibrillator element in the compartment in the responsive device.

14. The kit of claim 1, wherein the electronic connector component is selected from a group consisting of a USB cable, a cable wire, port adaptors, a Y-shaped cable, two USB connectors or BLUETOOTH.

15. The kit of claim 1, wherein the retrofitted computer includes a manual override, the manual over-ride providing the ability to administer a defibrillating shock from the defibrillator element, the manual override located on the computer.

16. The kit of claim 15, wherein the manual override is only accessed upon entering a password or key code into the retrofitted computer.

17. The kit of claim 1, wherein the responsive device includes software to provide instantaneous connection to the retrofitted computer.

18. The kit of claim 1, wherein the retrofitted computer comprises an assessment circuit that assesses whether the at least two electrode pads are properly attached to a person.

19. The kit of claim 1, wherein the defibrillator element is a fully automated defibrillator or a shock-advisory defibrillator.

20. The kit of claim 1, wherein the retrofitted computer comprises a shock control, the shock control requiring activation to deliver an electric shock when the defibrillator element is a shock-advisory defibrillator.

21. The kit of claim 1, wherein the retrofitted computer includes audio voice and visual prompts to guide a user through defibrillation of a person.

22. The kit of claim 1, wherein the defibrillator element determines if a person is in ventricular fibrillation.

23. The kit of claim 1, wherein the responsive device includes an external chip, the external chip required to access the defibrillator element.

24. The kit of claim 23, wherein to receive the external chip, a user must first complete a training program on CPR and defibrillation.

25. The kit of claim 1, wherein the defibrillator element provides low energy shocks of 120-200 joules.

\* \* \* \* \*